(12) United States Patent
Beckmann et al.

(10) Patent No.: US 6,232,063 B1
(45) Date of Patent: May 15, 2001

(54) CO-DOMINANT GENETIC DIAGNOSIS TEST

(75) Inventors: Jacques S. Beckmann, Charenton; Nathalie Bourg, Corbeil-Essonnes, both of (FR)

(73) Assignee: Association Francaise Contre les Myopathies, Paris (FR)

( * ) Notice: Subject to any disclaimer, the term of this patent is extended or adjusted under 35 U.S.C. 154(b) by 0 days.

(21) Appl. No.: 09/000,148

(22) PCT Filed: Jul. 12, 1996

(86) PCT No.: PCT/FR96/01093

§ 371 Date: Aug. 4, 1998

§ 102(e) Date: Aug. 4, 1998

(87) PCT Pub. No.: WO97/06276

PCT Pub. Date: Feb. 20, 1997

(30) Foreign Application Priority Data

Aug. 7, 1995 (FR) .................................................. 95 09586

(51) Int. Cl.$^7$ ....................................................... C12Q 1/68
(52) U.S. Cl. ............................. 435/6; 435/91.1; 435/91.2; 536/24.31; 536/24.33; 536/320.1; 424/85.8
(58) Field of Search ................... 435/6, 91.2; 536/24.31, 536/24.33, 320.1; 424/85.8

(56) References Cited

U.S. PATENT DOCUMENTS 5,853,989 * 12/1998 Jefferys et al. ........................... 435/6

* cited by examiner

*Primary Examiner*—W. Gary Jones
*Assistant Examiner*—Janell Taylor
(74) *Attorney, Agent, or Firm*—McKenna & Cuneo, LLP

(57) ABSTRACT

A method for detecting the homozygous or heterozygous state of mutations assumed to be present in a nucleic acid by simultaneously using two primer pairs. The two different primer pairs lead to the production of amplified fragments of different sizes, and the number and quality of the amplified bands enables homozygous and heterozygous items to be distinguished on the basis of said mutation.

16 Claims, 3 Drawing Sheets

CO-DOMINANT GENETIC DIAGNOSIS TEST

Figure 1:
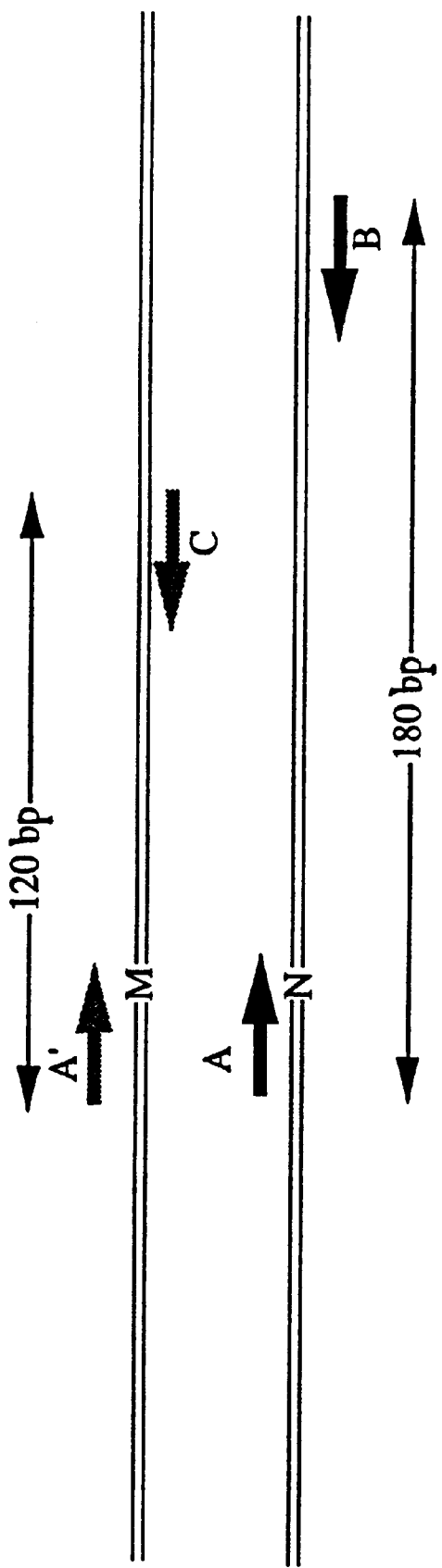

The present invention relates to a co-dominant genetic diagnosis test, i.e., a test to distinguish homozygous and heterozygous individuals for a polymorphous allele in a population.

A rapid and effective method for detecting a point mutation at the genomic DNA level is essential to the identification of polymorphisms both for genetic studies and predicting a risk of disease linked to that polymorphism, and for the study of the molecular bases for hereditary diseases. It is also essential for the development of a genetic diagnosis test.

In the remainder of the text, the term "point mutation" is used to encompass a change in a sequence, be it a nucleotide transition, transversion, deletion or addition; more generally, this includes transitions, transversions, deletions or additions of 1 to 6 nucleotides.

More generally, such a type of rapid, effective and inexpensive detection method can be applied to detecting mutations in any living organism, be it a micro-organism, animal or plant, the method being of particular importance for diploid organsims. Such a type of detection is applicable to the fields of agriculture and food, medicine or veterinary diagnoses, or to animal or plant selection.

PCR (1) represented a great advance for genomic DNA analysis. That technique enables genetic diseases to be diagnosed when combined with other techniques (2, 3, 4, 5, 6, 7, 8, 9); it may be a combination of PCR and direct sequencing (2, 3, 4, 10) or the allele specific oligonucleotide (ASO) technique (11, 12).

In some cases, the appearance of a point mutation can create or destroy a recognition site in a restriction enzyme (13); the presence or absence of the restriction site can be used to cany out diagnoses, as has recently been demonstrated for sickle-cell anaemia diagnosis (7); in the same way, a restriction polymorphism can be linked to a non characterised mutation which enables a diagnosis to be made in families by analysis of that polymorphism after amplification. A number of techniques have been developed with the aim of enabling such mutations to be detected by combining PCR with other types of reaction. These are in particular:

the technique known as PCR amplification of specific alleles (PASA), a modification of the PCR technique using either an oligonucleotide primer which hybridises with the wild allele but does not hybridise with the mutant allele, or vice versa: the amplified product will thus be specific for the allele for which the primers have been selected and amplification is thus ineffective if the primer has not hybridised with the corresponding allele (14);

HEIM et al. (15) used a set of different primers to amplify the two alleles, the amplifications being followed by allele specific PCR;

SCHUSTER et al. (16) combined asymmetric PCR with allele specific PCR using a set of 3 oligonucleotide primers in a single reaction mixture to detect a point mutation in the apoB gene; however, for recessive diseases, that (simple) technique cannot distinguish individuals carrying a single mutated allele from diseased individuals with two mutated alleles.

Other methods have been used, particularly for demonstrating the creation of a restriction site by mutation from an amplification product. That technique has been used to detect haemophilia B (17) or haemophilia A (18).

None of the diagnosis test techniques described is suitable for widespread use in a population as they require either lengthy, complex, and expensive steps which necessitate the exercise of a high level of technical skill, or they cannot differentiate homozygous from heterozygous individuals; other techniques such as allele specific oligonucleotides are dominant types and cannot differentiate a homozygous individual from a heterozygous individual having one normal allele and one mutated allele. For genetic diagnosis, in particular predicting the risk of genetic disease in given populations, it is extremely important to be able to identify those two populations without resorting to complex and expensive techniques.

The present invention can overcome the disadvantages of the different techniques described in the literature, and in particular it avoids the use of radio-elements; it concerns a method of detecting the homoygous or heteroygous state of a mutation assumed to be present in a nucleic acid, characterised in that two nucleic acid amplifications are used, the two amplifications respectively requiring the use of at least two primer pairs:

the first pair being constituted by an oligonucleotide which is specific for the wild allele (A) and a second oligonucleotide (B) which is different from (A);

the second pair being constituted by an oligonucleotide which is specific for the mutant allele (A') and a second oligonucleotide (C), which is different from (A') and from (B);

the difference in length between the amplified fragments between (A) and (B) and between (A') and (C) being sufficient to be detected by conventional analysis techniques.

These two amplifications are simultaneous.

The term "simultaneous" here means that the reaction products are simultaneously analysed using conventional methods, in particular analytical or preparative DNA separation, especially polyacrylamide gel or agarose gel electrophoresis; however, it will be clear to the skilled person that any other method of analysing the size of the amplified fragments (such as chromatography) can be considered as an equivalent means in the method of the invention.

The two amplification reactions can be carried out either in two different reaction mixtures if (A) and (A') are complementary to the same DNA chain, or they can be carried out in the same reaction mixture if (A) and (A') are complementary to the (+) and (−) strands of the DNA respectively.

In particular, the differences in the lengths can be detected by the existence of two different bands after agarose gel electrophoresis migration, for example; however, it will be clear that when detection methods become more sensitive, the differences in the lengths between the amplified fragments can be reduced.

More generally, any technique for amplifying a DNA sequence which comprises the use of at least two primers and a polymerase to synthesise the complementary sequence between the two primers, whatever the improvements thereto, can be used to implement the invention which resides in the simultaneous use of two different primer pairs and simultaneous visualisation of the PCR products.

The two primer pairs, (A) and (B) and (A') and (C), can be symmetrical or inverted, in other words (A) and (A') are hybridisable with the same strand of the double helix, and (B) and (C) with the other strand, or in contrast, the (A) (B) pair and the (A') (C) pair can be inverted, i.e., (A) and (A') are hybridisable with complementary strands of the DNA chain, like (B) and (C).

In the first variation, the two amplifications carried out by the two primer pairs must be carried out separately, then the reaction products must be mixed for analysis using conventional methods.

In contrast, in the second variation, the reaction products can be mixed from the start, since amplification between (A) and (C) cannot occur. However, in the latter case, primers (A) and (A') must have a sufficiently different sequence to avoid unwanted hybridisation between (A) and (A') in the reaction mixture. The only requirement is that (A) and (A') carry the nucleotide corresponding to that for which the mutation is sought.

Finally, this technique can be used whatever the DNA-containing organism, be it a micro-organism, bacterium, virus, animal or plant; however it is of particular importance for diploid or polyploid organisms.

The usefulness of this novel technique has been demonstrated by identifying a mutation in Amish populations from southern Indiana carrying a gene coding for a protein involved in a recessive autosomal disease: limb-girdle muscular dystrophy.

While the conventional PCR method has proved to be extremely powerful for amplifying target sequences, particularly in complex genomes, small unwanted bands due to artefacts often appear in the band spectra obtained after amplification. This is often interpreted as a priming error in the target chain; further, R. H. DON (19) has developed a technique known as "Touchdown" which can eliminate these artefacts far more rigorously than prior techniques which were essentially adjustments to the concentration of magnesium or an increase in the hybridisation temperature of the primer with the DNA. The Touchdown method exploits the exponential nature of PCR and can begin above the standard hybridisation temperature: the reaction temperature starts 5° C. to 10° C. above this hybridisation temperature (for example 65° C.) then decreases regularly by 1° C. to 2° C. per cycle until the standard hybridisation temperature is obtained by this technique; any difference in Tm between correct and incorrect annealing gives an advantage of the correct product over the incorrect product, everything else being equal. Thus a difference of 5° C. can give a $4^5$ times advantage (19).

In order to avoid the risk of errors inherent to amplification techniques, in the method of the invention the amplified fragments preferably have lengths which are respectively in the range 50 to 200 nucleotides; further, and so that identification of the amplified segments between (A) and (B) and (A') and (C) is not ambiguous, the difference in length is preferably at least 10%. The method of the invention is particularly important for detecting point mutations as defined above.

The invention also concerns a kit for diagnosing assumed homozygous or heterozygous point mutations and is characterised in that it contains at least:

a) a heat stable polymerase;

b) a first primer pair constituted by an oligonucleotide (A) which is specific for the wild allele and a second specific oligonucleotide (B), distinct from (A);

c) a second primer pair constituted by an oligonucleotide which is specific for the mutant allele (A') and a second oligonucleotide (C) distinct from (A), the size of the amplified fragments between primers (A) and (B) and primers (A') and (C) preferably differing by at least 10%.

In addition to the above four primers (A), (A'), (B), (C), the kit of the invention contains all of the elements required to enable PCR amplification, or any improved method derived therefrom, in particular the "Touchdown" PCR method, to be carried out.

More particularly, the kit of the invention can be used to detect or identify the homozygous or heterozygous state of point mutations, whether these mutations are transitions or transversions. Using these two simultaneous amplifications results in a co-dominant diagnosis test the results of which can be interpreted more easily than any prior art procedures.

The diagnosis kit of the invention can also be used in the field of human or animal health and in any other sector such as the environment, plant breeding or the agriculture and food industry for which detection and monitoring of the healthy or infectious state of the medium may be important.

The diagnosis test can also be applied to an animal or plant selection process.

The following non limiting examples and the accompanying figures illustrate the performance of the invention in detecting a point mutation in the LGMD2E gene coding for the protein involved in a type of limb-girdle muscular dystrophy.

FIG. 1 is a diagram which illustrates the system of the invention when the primer pairs are symmetrical. In this Figure, N is the normal allele and M is the mutant allele. The arrows point in the 5'–3' direction and represent the primers.

Figure 2:
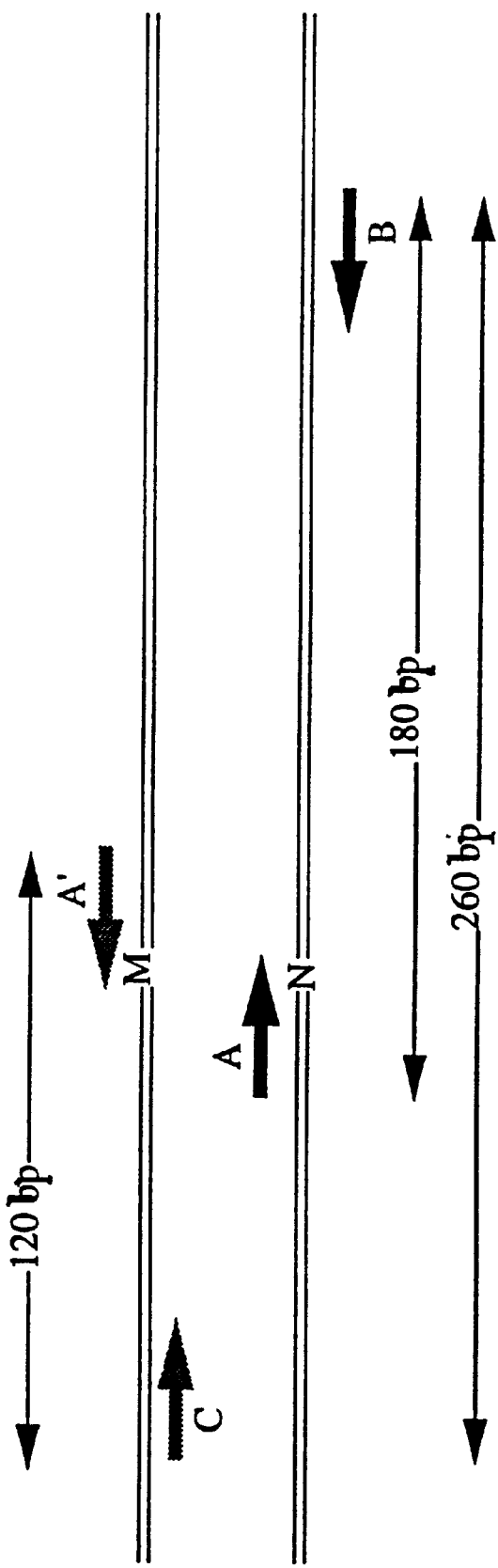

FIG. 2 is a diagram which illustrates the system of the invention when the primer pairs are asymmetrical. N and M and the arrows have the same meanings as in FIG. 1.

Figure 3:
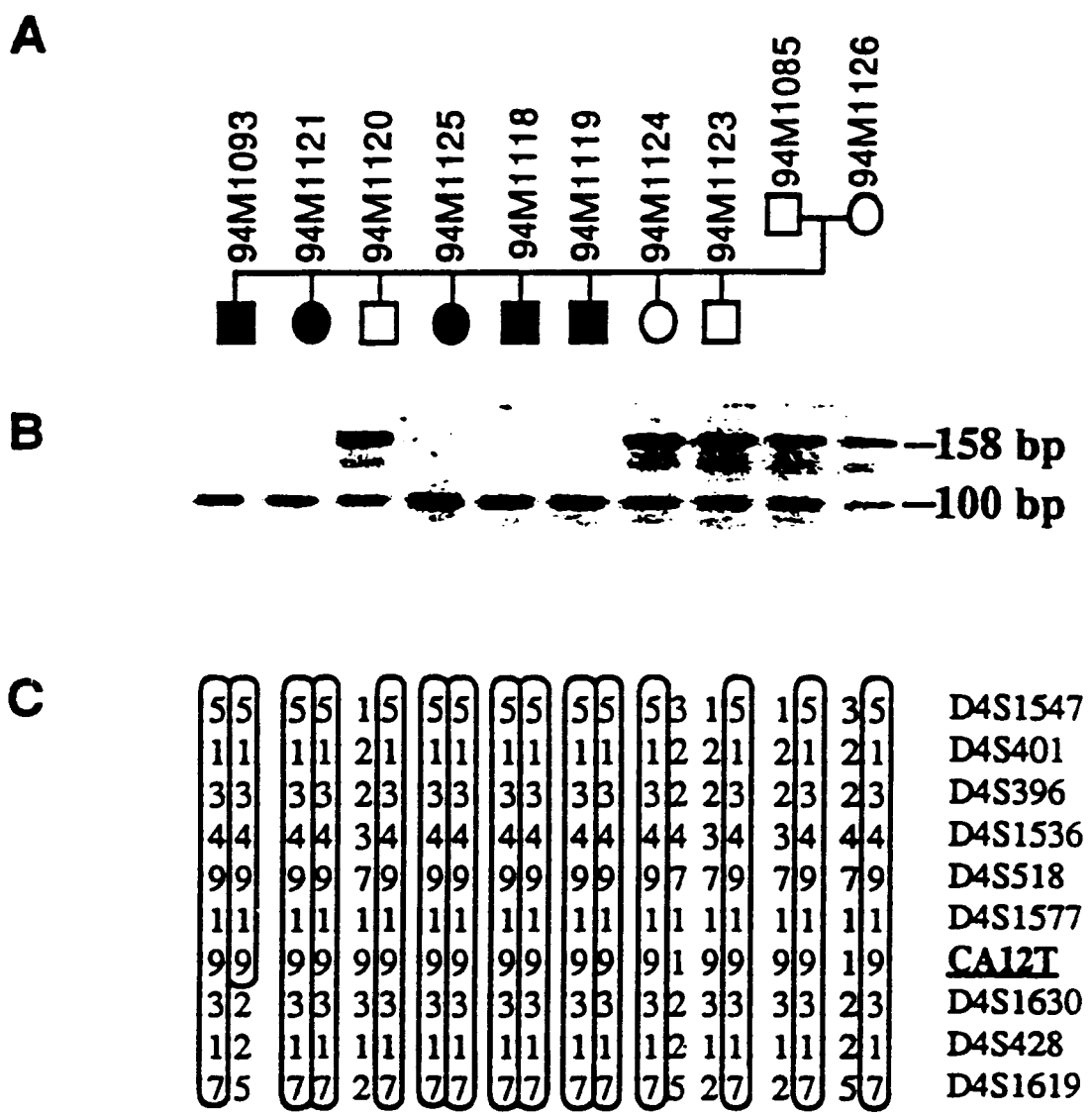

FIG. 3 shows the segregation of the threonine to arginine substitution in an Amish population. In the figure, line A shows the pedigree of family A620 in which affected or healthy individuals are indicated by black or white symbols respectively. The term "healthy" means that the individuals may be non carriers or carriers of heterozygotes; B shows the result obtained for agarose gel electrophoresis of mixtures of the amplification products using "Touchdown" PCR of fragments of 100 and 158 base pairs respectively; C shows the segregation of haplotypes on chromosome 4 in the family; chromosomes carrying the mutation are ringed, and CA12T represents the intragenic micro-satellite.

IMPLEMENTATION EXAMPLE

FIGS. 1 and 2 illustrate the technology of the invention. In this example, all the primers are 20 nucleotides in length.

a) Primer Pairs (A) (B) and (A') (C) are Symmetrical

This case is shown in FIG. 1.

In the figure, the first primer pair (A) (B) specific to the normal allele can produce a 180 bp amplification product; primer (B) is located 140 bp below the nucleotide where the mutation is located and primer (A) contains that nucleotide at its 3' extremity.

The second primer pair (A') (C), which serves to identify the mutant genotype, has a primer identical to primer (A), but in place of the normal 3' nucleotide it has mutant nucleotide M. The other primer (C) below the mutation is selected so that the product obtained by PCR is significantly different from product (A) (B), in this case 120 bp.

When the amplification products are mixed after the PCR phase then deposited on 4% agarose gel containing ethidium bromide in a TBE1×buffer, two bands are obtained in the same trace when the starting sample contains a normal allele and a mutant allele. Thus the conventional "dominant" diagnosis system with a "yes/no" type response for each of the PCR reactions has been transformed into a readily interpretable co-dominant system.

Homoygotes produce only a single band of 120 or 180 bp depending on whether the homozygote is mutated or normal.

b) Antisymmetrical Primers

FIG. 2 illustrates this case. It can clearly be seen that the primer pairs (A) (B) and (A') (C) lead, as before, to amplification products of 120 bp for the mutant and 180 bp for the wild.

In this figure, it can be seen that when PCR amplification is carried out in a single reaction medium containing the 4 primers, a mixture of 3 amplification products is obtained: 2 products corresponding to the wild and mutant alleles, of respectively 180 bp and 120 bp, and a product corresponding to amplification between primers (B) and (C) with a length of 260 bp.

Depositing the products of the PCR on 4% agarose gel containing ethidium bromide produces three bands corresponding respectively to the 120, 180 and 260 bp products when the amplified DNA is heterozygous and carries the two alleles N and M.

If in contrast, the DNA is homozygous for the normal allele, the amplification products will comprise only 2 bands of 180 and 260 bp.

Finally, if the DNA is a mutant homozygote, the reaction product will contain 2 bands of 120 and 260 bp.

This diagnosis system thus has all of the advantages of other systems using PCR, namely sensitivity, non radioactive, automatable, etc. . . . , but above all it has the additional advantage of transforming dominant markers into co-dominant markers.

EXAMPLE OF USE

Identification of a Mutation in Amish Patients Carrying LGMD2E a) Selection of Families An analysis was carried out on six families, already described in the prior art (20), comprising 52 individuals, 13 of whom were affected. 5 additional families were also included, comprising 39 individuals in total, 13 of whom were affected.

When seeking to identify the protein involved in these families, Northern blot analyses were carried out on the total RNA isolated from a skeletal muscle biopsy to determine whether the size or quantity of messenger RNA of the LGMD2E gene which was produced had been affected. The translated RNA population, with a size of 4.4 Kb was normal in quantity and size both in samples from the affected patients and from the healthy controls. This strongly suggested that the mutation was probably due to a point mutation as defined above. In order to verify this, cDNA fragments of the LGMD2E gene were amplified after reverse transcription from total RNA prepared from six muscle biopsies. The RT-PCR products were sequenced and a simple transversion of C to G at nucleotide 461 was detected in the two patients with two mutated alleles. The codon change is ACA to AGA and results in a substitution of threonine by arginine corresponding to a missense mutation in residue 151.

Segregation of this mutation was studied in this family and in other families carrying limb-girdle muscular dystrophy then amplifying the corresponding fragment by the Touchdown PCR technique described above.

b) Touchdown PCR 50 ng of DNA underwent the touchdown PCR procedure (19) in 50 µlitres of reaction mixture containing 10 mM of Tris HCl, pH 8.8, 50 mM KCl, 1.5 mM $MgCl_2$, 0.1% Triton X-100, 200 mM of each dNTP, 100 ng of each primer, and 2 units of Taq polymerase (Perkin-Elmer). After denaturing at 96° C. for 5 minutes, the first amplification step was carried out as follows: 40 seconds (sec) at 94° C. then 30 sec at 63° C. (this constituting a cycle) with a reduction of 1° C. every 2 cycles from 63° C. to 59° C. In total, 10 PCR cycles were carried out with two cycles at each temperature of 63° C. to 59° C. inclusive. The second step was carried out in 25 additional amplification cycles consisting of 40 sec at 94° C. and 30 sec at 58° C.

Primer Pairs Used

First primer pair:

a) Type AB primer pair to amplify the wild allele:

T461: 5'-GTTTTTCAGCAAGGGACAAC-3' ml: 5'-CTTTTCACTCCACTTGGCAA-3'.

Second primer pair to amplify the mutant allele:

A461: 5'-GTTTTTCAGCAAGGGACAAG-3' m3: 5'-TATTTTGAGTCCTCGGGTCA-3'

It should be noted that in T461, the G at the 3' end has been substituted by C at the 3' end corresponding to a transversion of C to G in the cDNA sequence.

The amplification products were analysed on 4% agarose gel electrophoresis stained with ethidium bromide.

c) Results

The results are shown in part B of FIG. 1, the annotation of which has been given above. The difference in the sizes of the amplified segments was 58 base pairs, knowing that the amplification products of the T461/ml pair was 100 base pairs and that of the A461/m3 pair was 158 base pairs.

Analysis of FIG. 1 shows that parents with a normal phenotype were heterozygous since the amplification product contained the two types of fragments. Clearly, if one of these individuals was normal homozygous, the profile obtained after this group of operations would comprise only bands corresponding to a molecular weight of 158 base pairs.

Thus for the first time, the technology of the invention can unambiguously distinguish the homozygous or heterozygous state of a mutation in a population, avoiding complex enzymatic digestion or restriction site creation, for example. It is rapid and avoids experimentation using radio-elements.

Detection of heterozygotes has grown in importance in the field known as predictive medicine: for recessive sex-linked diseases, the possibility of detecting carrier females in families at risk represents a considerable advance. Regarding dominant diseases with delayed expression, carriers of the genetic trait are potential patients and this type of analysis can detect the risk whatever the penetrance of the defect and its degree of expressivity. In this case, the method of the invention enables pre-symptomatic diagnosis to be carried out, i.e., before the appearance of the first signs of any disease.

Finally, it will be clear to the skilled person that if the disease or, more generally, the phenotype sought, results from a combination of different point mutations, the principle of amplification using two primers and a heat stable polymerase to give amplification products with different sizes for each allele allows for combination of a plurality of these primer pairs provided that the amplification products each have a defined size, which is different from one product to another, and are visualisable.

BIBLIOGRAPHY

1. Saiki, R. K., Gelfand, D. H., Stoffel, S., Scharf, S. J., Higuchi R., Horn, G. T., Mullis, K. B. and Erlich, H. A. (1988) Science 239 487–91.
2. Newton, C. R., Kaisheker, N., Graham, A., Powell, S., Grammack, A., Riley, J. and Markham, A. F. (1988) Nucl. Acid. Res. 16 8233–8243.
3. Stoflet, E. S., Koeberl, D. D., Sarkar, G. and Sommer, S. S. (1988) Science 239 491–94.
4. Engelke, D. R., Hoener, P. A. and Collins, F. S. (1988) Proc. Nat. Acad. Sci. USA. 85 544–548.
5. Bruun Petersen, Kolvraa, S., Bolund, L., Bruun Petersen, G., Koch, J. and Gregersen, N. (1988) Nucl. Acid. Res. 16 352.

6. Bugawan, T. L., R. K., Levenson, C. H., Watson, R. M. and Erlich, H. A. (1988) Biotechnology 6 943–947.
7. Chehab, F. F., Doherty, M., Cai, S., Kan, Y. W., Cooper, S. and Rubin, E M. (1987) Nature 329 293–294.
8. Kogan, S. C., Doherty, M. and Gitschier, J. (1987) New Engl. J. Med 317 985–990.
9. Levinson, B., Janco, R., Phillips, J. and Gitschier J. (1987) Nucl. Acid. Res. 15 9797–9805.
10. Wong, C., Dowling, C. E., Saiki, R. K., Higuchi, R. G., Erlich, H. A. and Kazazian, H. H. (1987) Nature 330 384–386.
11. Connor, B. J., Reyes, A. A., Morin, C. Itakura, K., Teplitz, R. L. and Wallace, R. B. (1983) Proc. Natl. Acad. Sci. USA. 80 278–282.
12. Orkin, S. H., Markham, A. F. and Kazazian, H. H. (1983) J. Clin. Invest. 71 775–779.
13. Southern, E. M. (1975) J. Mol. Biol. 98 503–517.
14. Sommer S. S. et al (1989) Mayo Clim. Proc 64;1361–1372.
15. Heim, M. et al (1990) Lancet. 336: 529–532.
16. Schuster, H. et al (1992) Analytical Biochemistry 204: 22–25.
17. Mttsushita, T. et al (1991) Thrombosis Research 63: 355–361.
18. Pattinson J. K. et al (1990) British Journ. of Haematology 75: 33–77.
19. Don, R. H. et al (1991) Nucl. Ac. Research 19:4008.
20. Allamand, V. et al (1995) Human Molecular Genetics 4:459–64.

What is claimed is:

1. A method for detecting the homozygous or heterozygous state of mutations present in a nucleic acid, said method comprising the steps of:
   (1) amplifying two nucleic acids using a polymerase and at least two primer pairs wherein:
      a first primer pair consists of an oligonucleotide (A) which is specific for a wild allele and a second oligonucleotide (B), and
      a second primer pair consists of an oligonucleotide (A') which is specific for a mutant allele and a second oligonucleotide (C);
         wherein there is a difference in length between the amplified fragments between (A) and (B) and between (A') and (C) respectively; and
   (2) detecting said nucleic acid fragments.

2. The method according to claim 1, wherein primer (A) of the first pair hybridizes with one DNA strand, and primer (A') of the second pair hybridizes with the complementary strand.

3. The method according to claim 1, wherein primer (A) of the first pair hybridizes with one DNA strand, and primer (A') hybridizes with the same DNA strand.

4. The method according to claim 1, wherein amplification is carried out by an amplification method using at least two primers and a polymerase.

5. The method according to claim 1, wherein the mutations are point mutations.

6. The method according to claim 1, wherein the nucleic acid in which a mutation is detected originates from a human, an animal, or from a human or animal portion.

7. The method according to claim 1, wherein the nucleic acid in which the existence of a mutation is detected originates from a plant or a portion thereof.

8. A diagnosis kit for one step detection of homozygous or heterozygous mutations in a nucleic acid, consisting of at least:
   a) a heat stable polymerase;
   b) a first primer pair constituted by an oligonucleotide (A) which is specific for the wild allele and a second oligonucleotide (B);
   c) a second primer pair constituted by an oligonucleotide (A') which is specific for the mutant allele and a second oligonucleotide (C); wherein the size of the amplified fragments between primers (A) and (B) and primers (A') and (C) have a difference which is detectable.

9. The kit according to claim 8, wherein the size difference between the amplified fragments is at least 10%.

10. The kit according to claim 9, wherein said kit further contains elements enabling amplification by PCR or any derivative method.

11. The kit according to claim 9, wherein the assumed mutations for diagnosis are point mutations.

12. The diagnosis kit according to claim 8, for detecting genetic mutations in man or in animals.

13. The diagnosis kit according to claim 8, for detecting genetic mutations in plants or portions thereof.

14. The diagnosis kit according to claim 8, for animal or plant selection.

15. The method according to claim 4, wherein said amplification method is "Touchdown" PCR.

16. The method according to claim 10, wherein said amplification method is "Touchdown" PCR, using at least two primers.

* * * * *